United States Patent [19]

Schaffar et al.

[11] Patent Number: 5,683,562
[45] Date of Patent: Nov. 4, 1997

[54] PLANAR SENSOR FOR DETERMINING A CHEMICAL PARAMETER OF A SAMPLE

[75] Inventors: Bernhard Schaffar; Heinz Kontschieder; Andreas Dolezal; Christoph Ritter, all of Graz, Austria

[73] Assignee: AVL Medical Instruments AG, Schaffhausen, Switzerland

[21] Appl. No.: 528,250

[22] Filed: Sep. 14, 1995

[30] Foreign Application Priority Data

Sep. 14, 1994 [AT] Austria ................ A1760/94

[51] Int. Cl.$^6$ .................................................. G01N 27/26
[52] U.S. Cl. ...................... 204/403; 427/2.31; 427/243; 204/282
[58] Field of Search ....................... 204/400, 403, 204/412, 282; 427/2.12, 2.11, 118, 102, 103, 125, 126.1, 555, 231, 243; 436/806; 435/217

[56] References Cited

U.S. PATENT DOCUMENTS

| | | | |
|---|---|---|---|
| 4,073,713 | 2/1978 | Newman | 204/403 |
| 4,306,877 | 12/1981 | Lubbers | 204/400 |
| 4,568,518 | 2/1986 | Wolfbeis et al. | 427/2.12 |
| 4,938,860 | 7/1990 | Wogoman | 204/403 |
| 5,120,420 | 6/1992 | Nankai et al. | 204/403 |
| 5,126,034 | 6/1992 | Carter et al. | 204/403 |
| 5,264,104 | 11/1993 | Gregg et al. | 204/403 |
| 5,326,449 | 7/1994 | Cunningham | 204/403 |
| 5,387,329 | 2/1995 | Foos et al. | 204/403 |

FOREIGN PATENT DOCUMENTS

| | | | |
|---|---|---|---|
| 57-122797 | 7/1982 | Japan . | |
| 62-075346 | 4/1987 | Japan . | |
| 63-050748 | 3/1988 | Japan . | |
| 93/13408 | 7/1993 | WIPO | 204/400 |

OTHER PUBLICATIONS

U. Bilitewski et al., "Enzyme Electrodes for the Determination of Carbohydrates in Food" in *Sensors and Actuators B*, 15 (1993) 113–114.

Derwent and JAPIO abstracts of JP63050748 (Izeki Masahiro) Mar. 3, 1988.

Derwent and JAPIO abstracts of JP62075346 (Ichiro et al.) Mar. 7, 1987.

Derwent and JAPIO abstracts of JP57122797 (Tishio et al.) Jul. 30, 1982.

*Primary Examiner*—Kathryn L. Gorgos
*Assistant Examiner*—Alex Noguerola
*Attorney, Agent, or Firm*—Watson Cole Stevens Davis P.L.L.C.

[57] ABSTRACT

A planar sensor for determining a chemical parameter of a sample, includes a substrate whose surface is at least partly plane and is provided with at least one potentiometric or amperometric and, possibly, an optical transducer, and one or more biochemical components. The transducer and the biochemical component are provided on the surface of the substrate, or at least part of the surface, as a sensor spot, and a cover membrane surrounding this sensor spot, is heat welded to the surface of the substrate. Those sensor spots that include a potentiometric or amperometric transducer are in contact with a strip conductor attached to the plane surface of the substrate and the thermal seal of the cover membrane is interrupted where the conducting strips lead away from the sensor spots.

20 Claims, 5 Drawing Sheets

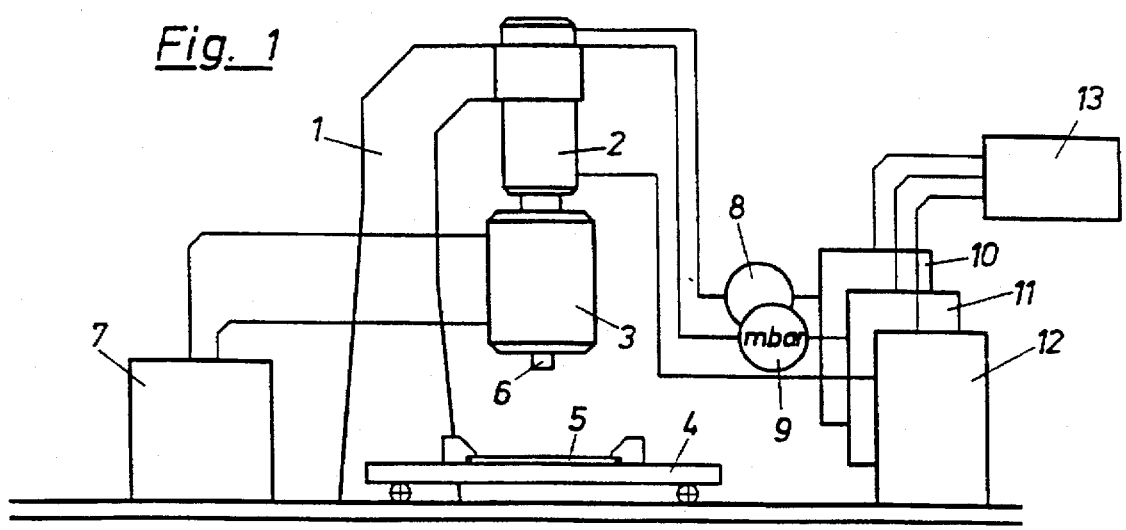
Fig. 1
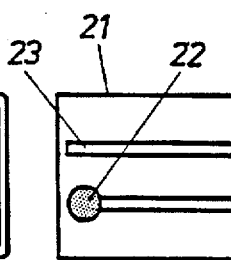 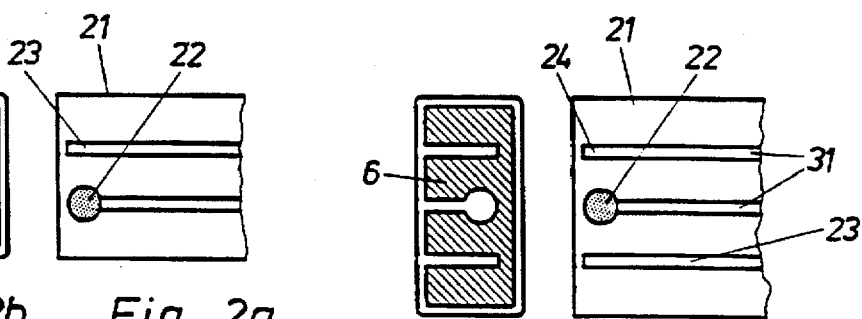
Fig. 2b    Fig. 2a        Fig. 3b    Fig. 3a
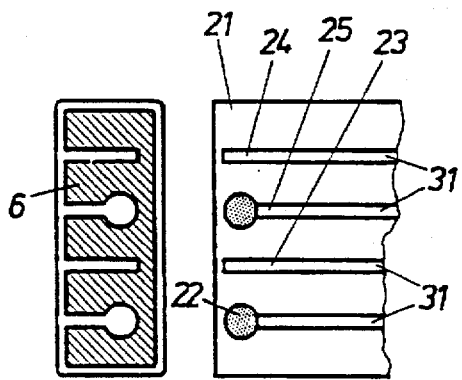 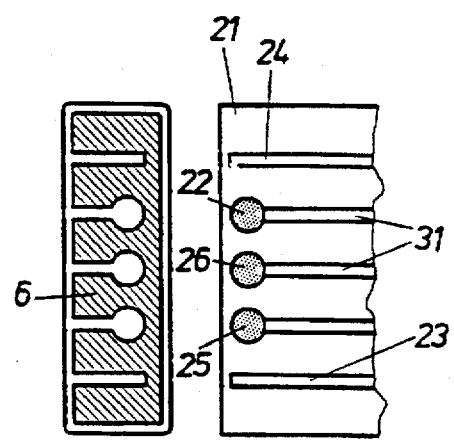
Fig. 4b    Fig. 4a        Fig. 5b    Fig. 5a

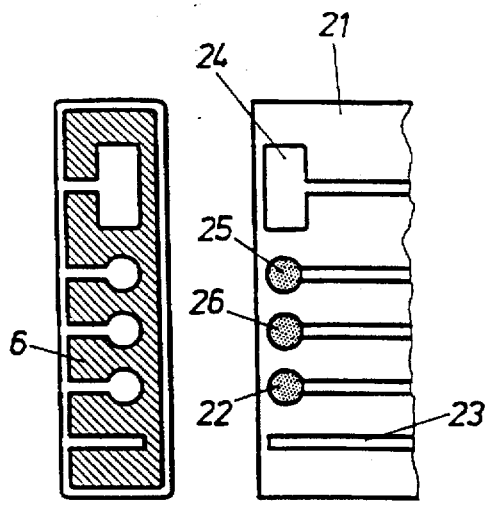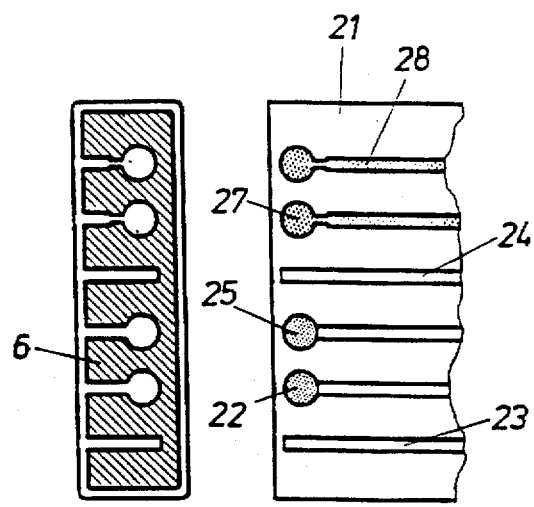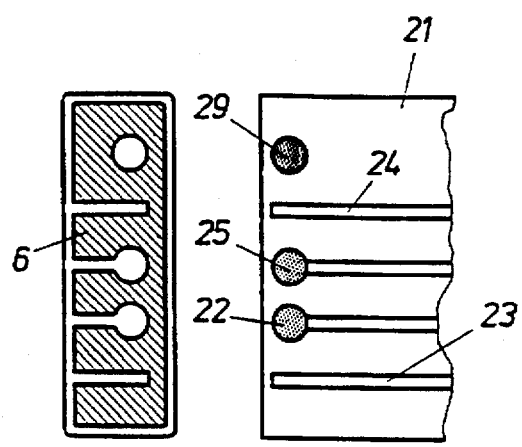
Fig. 6b    Fig. 6a    Fig. 7b    Fig. 7a
Fig. 8b    Fig. 8a

PLANAR SENSOR FOR DETERMINING A CHEMICAL PARAMETER OF A SAMPLE

BACKGROUND OF THE INVENTION

The invention relates to a planar sensor for determining a chemical parameter of a sample, comprising a substrate whose surface is at least partly plane and is provided with at least one potentiometric or amperometric and, possibly, an optical transducer, and one or more biochemical components, and with a cover membrane on the side facing the sample, the transducer and the biochemical component being provided on the surface of the substrate, or at least part of the surface, as a sensor spot, and the cover membrane surrounding this sensor spot and sealing it off.

Such sensors are predominantly used in applications of medical technology, biotechnology and chemical food analysis. The biochemical component of the sensor may be a microorganism, an enzyme, an antibody or antigen, or DNA/RNA, for example. The term transducer or transducer layer means the total of all those elements that convert the originally material information of the biochemical system into a current signal (amperometric), voltage signal (potentiometric), or light signal (photometric). An optical transducer may be provided with a fluorescent dye whose optical properties change with the $O_2$ concentration or the pH, for instance. In potentiometric sensors the ion-selective membrane between the strip conductor and the enzyme layer may be regarded as potentiometric transducer.

The cover membrane attached on the side facing the is sample in useful limiting diffusion, if the sample concentration to be determined surpasses the analytic measuring range of the sensor, in addition to offering mechanical protection of the biochemical component, and a certain amount of biocompatibility.

The cover membrane of such sensors is porous, or rather, made of porous material, pore diameters ranging from 100–5,000 angstroms, depending on the particular application. The pores in the cover membrane will permit contact between the material to be measured and the biological component underneath the cover membrane. With such sensors care should be taken during application of the cover membrane that the sensitive biological component is not destroyed or otherwise interfered with.

Another purpose of the cover membrane is to ensure that the prefabricated sensor spots, which can be produced quite cheaply on a large scale, adhere to the surface or in recesses of a substrate.

DESCRIPTION OF THE PRIOR ART

In "Sensors and Actuators B", 15 (1993), 113 (BILITEVSKY et al.) an enzyme electrode is described which is used for the detection of carbohydrates in foodstuffs. In this instance a polycarbonate membrane serving as a cover membrane is bonded to a planar sensor. For this purpose an adhesive is applied on a substrate with the use of a screen-printing technique, before the cover membrane is pressed into the adhesive by applying a vacuum. The air between sensor surface and polycarbonate membrane is permitted to escape by perforating the substrate before use. The adhesive is cured for five minutes at 120° C., during which time the sensor spot itself must be cooled in a special device. The disadvantage of this kind of planar sensor is that a number of different steps are necessary for its preparation, in particular the application and curing of the adhesive at comparatively high temperatures, which necessitate the cooling of the sensor spot as the biochemical component as a rule cannot endure such high temperatures. Another disadvantage is that monomers or oligomers or solvent molecules potentially emerging from the adhesive layer before curing could impair the biochemical component.

Another method of attaching a cover membrane to the surface of such biosensors is described in U.S. Pat. No. 4,073,713. In this instance a polycarbonate membrane is pressed onto the sensor surface by means of an 0-ring. On the polycarbonate membrane the enzyme is immobilized on the sensor side, or a second membrane is affixed thereto. This technique is less suitable for use with planar sensors, nor does it permit miniaturization of the sensors, which would be a desirable feature in many applications. In addition, semi- or fully automated manufacturing processes are made difficult and expensive.

U.S. Pat. No. 5,326,449 discloses a sensor with a multilayer or composite membrane which is suitable for glucose measurement among others. The composite membrane of this amperometric sensor is made up of a porous membrane containing a biochemically active component, such as a protein, in immobilized form, and of at least one other membrane. In a first embodiment the composite membrane is bonded to the substrate by ultrasonic welding. In another variant of U.S. Pat. No. 5,326,449 the proposal is put forward that the sensor membrane be covered by a protecting membrane extending beyond its rim and being welded to the substrate outside of it. The substrate has an opening through which an electrically conductive element is passed for signal pick-up.

SUMMARY OF THE INVENTION

It is an object of the invention to propose a planar biosensor whose cover membrane can be attached on the side facing the sample by a fast and efficient process permitting semi- or fully automated mass production of such sensors in a simple way In the invention this object is achieved by providing that the sensor spots comprising a potentiometric or amperometric transducer be in contact with a strip conductor attached to the plane surface of the substrate, and the thermal seal of the cover membrane being interrupted where the conducting strips lead away from the sensor spots.

In the automated production of such planar sensors significant advantages are gained by positioning the entire sensing device including the strip conductors on one and the same side of the substrate, thus eliminating any bores or feedthroughs through the substrate. All essential components, such as strip conductors, reference and counterelectrodes as well as working electrodes can be attached by screen-printing or dispensing techniques. Moreover, specific tests have shown quite unexpectedly that by means of a heat stamp with recesses in those positions where the sensor spots are located or where the strip conductors lead away from the sensor spots, the heat load even on such temperature- sensitive biochemical components as the lactic oxidase enzyme, can be kept low enough to dispense with the additional cooling of the sensor spot while ensuring that the strip conductors remain intact. The heat stamp may be as hot as 200° C., for instance, in polycarbonate welding, and may be applied for a few seconds. By increasing the pressure applied during this process, both sealing time and sealing temperature may be reduced. Furthermore, the welding or sealing process may be restricted to individual spots or sections of the surface, which will further reduce the thermal load. The stamping tools can be designed to promote self-tightening of the cover membrane, which is an advantage, especially if short response times of the sensors are desired. By controlling the parameters of temperature, pressure and welding time the manufacturing process may be automatized to permit mass-production. The sensor of the invention has no glued joints and thus none of the disadvantages that are usually encountered when adhesive chemicals are applied or cured, or when a change in the diffusion properties of the cover membrane takes place which is induced by the use of adhesives.

According to the invention, a method of producing a planar sensor for determining a chemical parameter of a sample may be characterized by the following steps:

(a) attaching a strip conductor to at least part of the surface of a substrate, (b) applying a potentiometric or amperometric transducer layer onto one end of the strip conductor, (c) affixing at least one biochemical component to the transducer layer, (d) covering at least the transducer layer and a surrounding area with a cover membrane being heat weldable to the substrate, (e) thermally sealing the cover membrane to the substrate in areas not covered by the transducer layer and the enzyme layer, the thermal seal being interrupted in the area of the strip conductor.

Instead of items (b) and (c) it is proposed in a variant of the invention that a polymer matrix be applied on one end of the strip conductor, and that the potentiometric or amperometric transducer and the biochemical component be immobilized on or in the polymer matrix, i.e., transducer layer and biochemical component be applied together as one layer.

For automation of the process the cover membrane may be unwound from a roll of tape, stretched over the surface of the substrate and thermally welded to the substrate by means of a heat stamp. The seals obtained with this method may be continuous or in individual spots only.

The invention would also permit thermal welding of the cover membrane to the substrate by means of a laser technique.

The sealable cover membrane may be made of thermoplastic material, preferably polycarbonate, polyurethane, polysulphone, or cellulose acetate, and the substrate of thermoplastic material, i.e., at least in the area where the cover membrane is sealed to it, preferably of polycarbonate, polysulphone, PVC, or plexiglass (PMMA).

In addition to the use of a conventional reference electrode (such as a calomel electrode), at least one sensor spot may be configured as a working electrode in a potentiometric or amperometric device, and, if applicable, at least one reference and/or counterelectrode may be provided on the surface of the substrate.

To obtain accurate checkpoints or reference points for measuring the invention proposes that at least two sensor spots be provided, one of them containing an active biochemical component and the other one the same component in a deactivated state. This will provide a compensation electrode.

According to the invention this arrangement will permit that the cover membrane covers the reference and/or counterelectrode and is sealed around them to the substrate, the seal being interrupted in the area of the strip conductors leading away from the electrodes. The cover membrane offers mechanical protection to the electrode surfaces, e.g., against the depositing of red blood cells.

Another preferable variant of the invention proposes that an additional sensor spot with an optical transducer be provided, which has an indicator layer with an optical indicator, and at least one layer with the biochemical component.

Finally, the invention would also permit that an additional sensor spot with a polymer matrix be provided, in or on which the optical indicator and the biochemical component are immobilized either chemically or physically.

DESCRIPTION OF THE DRAWINGS

The invention will be further described with reference to the accompanying drawings, in which FIG. 1 is a schematical representation of an apparatus for sealing the cover membrane to the substrate, FIGS. 2a to 8a show planar sensors in accordance with the invention, FIGS. 2b to 8b show the respective heat stamps or sonotrodes required.

DETAILED DESCRIPTION OF THE PREFERRED EMBODIMENTS

Figure 9:
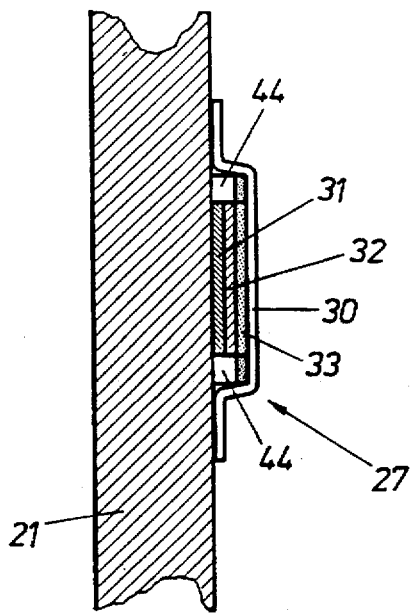
FIGS. 9 to 21 are sectional drawings of several variants of the planar sensors described by the invention.

In FIG. 1 an apparatus is shown which is used for sealing a cover membrane to the surface of a substrate of a planar sensor. This apparatus is made up of a toggle press 1, whose compressed air cylinder 2 will lower a temperature control block 3 down to a horizontally and vertically adjustable table 4. The table 4 has a mounting rack 5 for the substrate of the planar sensor. On the side of the temperature control block 3 facing the mounting rack 5 a heat stamp 6 is provided, whose die profile is described in more detail below, under the variants of the planar sensors. The temperature control block 3 is provided with a thermostat 7 for temperature control. Additional units include pressure gauges 8 and 9 for control of holding and sealing pressure, and timers 10 to 12 for control of the sealing time and for lifting and lowering the stamp 6. A central control unit for coordination of timers 10 to 12 has the reference number 13.

An apparatus for ultrasonic welding may be designed in a similar manner, using a sonotrode instead of the stamp 6.

The planar sensors in FIGS. 2a to 9a are shown in a view from above, without their cover layers. The substrate of each sensor variant has the reference number 21, and the different heat stamps shown in the corresponding FIGS. 2b to 9b each have the reference number 6. The heat stamp 6 is shown as a section cut along the recesses for the individual sensor spots and strip conductors, the hatched area corresponding to the actual die face of the respective stamp. If an ultrasonic welding technique is employed, the hatched area represents the active surface of the sonotrode. In the area of the strip conductors 31 leading away from the sensor spots the die face and thus the seal between membrane and substrate 21 is interrupted (see FIGS. 19 and 21). Other variants of heat stamps are possible, however, where there are additional recesses between individual sensor spots, or where stamping and sealing takes place only in isolated points around the sensor spots.

FIGS. 2a and 3a each show an amperometric biosensor, 22 being the working electrode, and 23 the reference electrode. The biosensor in FIG. 3a is additionally provided with a counterelectrode 24.

FIG. 4a shows an amperometric biosensor configured as a bisensor. In addition to a working electrode 22 with an active enzyme, a comparison electrode 25 with an inactive enzyme is positioned on the surface of the substrate 21.

FIG. 5a shows a substrate with two amperometric biosensors 22 and 26 with joint reference-, counter- and comparison electrodes 23 to 25. The working electrode 22 carries a first active enzyme, and the other working electrode 26 a second active enzyme, the signals from the two electrodes being obtained as difference signals relative to the comparison electrode 25.

FIG. 6a shows an arrangement similar to that of FIG. 5a, with an enlarged common counterelectrode 24.

In FIG. 7a a combination of amperometric and potentiometric biosensors is shown on a substrate. In addition to the amperometric working electrode 22 with a first active enzyme as described in the variants above, and the respective reference-, counter- and comparison electrodes 23 to 25, the substrate of FIG. 7a carries a potentiometric biosensor 27 and a potentiometric reference electrode 28.

In the variant shown in FIG. 8a a biosensor 29 is provided in addition to an amperometric working electrode 22 with an active enzyme and the respective reference-, counter- and comparison electrodes 23 to 25, the biosensor 29 containing a pigment or dye whose optical properties will change with the oxygen content, for example.

The electrodes 22, 25, 26, 27, 28 as well as the optode 29 of the variants described above are incorporated into the essentially plane or slightly curved surface of the substrate as so-called sensor spots, or rather, they are inserted as prefabricated elements into the recesses on the surface of the substrate.

The configuration of the different sensor spots and reference- and counterelectrodes is described in more detail below, with reference to FIGS. 9 to 21.

Figure 10:
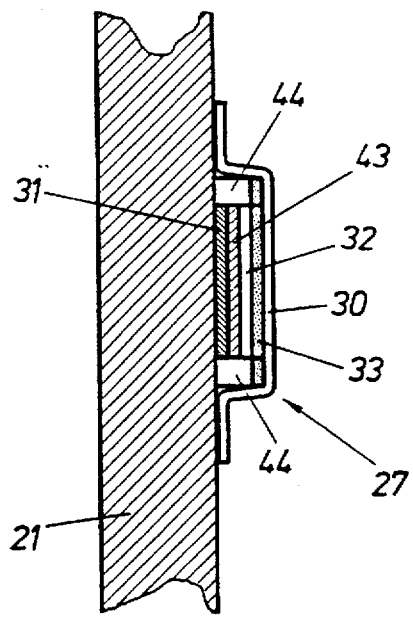
Figure 11:
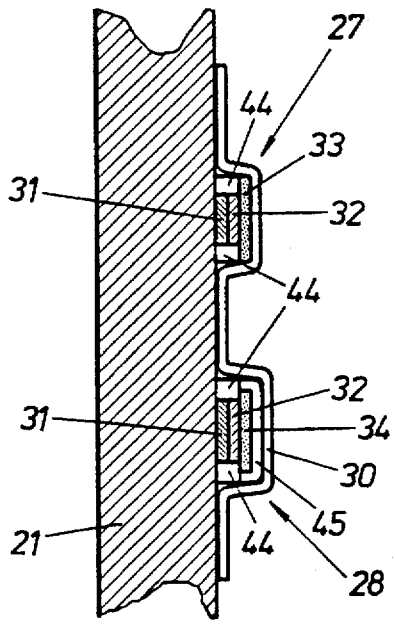
Figure 12:
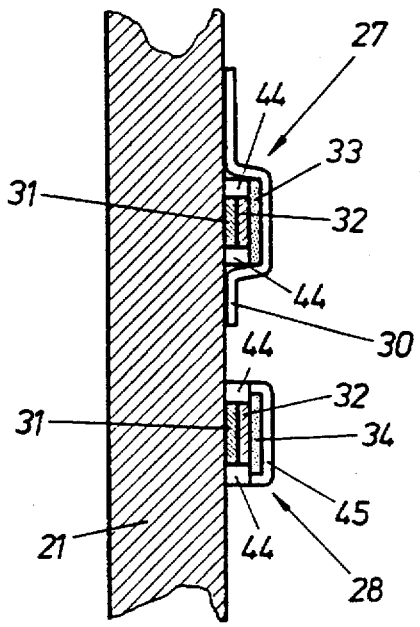

FIGS. 9 to 12 give variants of a potentiometric biosensor, comprising a substrate 21 with a sensor spot 27 (working electrode with an active enzyme), which is made up of a strip conductor 31, an ion-selective membrane 32 and an enzyme layer 33. The cover membrane is sealed around the sensor spot 27 to the substrate 21. An insulating layer 44, for instance made of polyurethane, is provided around the sensor spot and on top of the strip conductor. The variant of FIG. 10 differs from that of FIG. 9 only in that a contact layer 43 is provided between the strip conductor 31 and the ion-selective membrane 32. In the variants of FIGS. 11 and 12 the sensor strip additionally carries a potentiometric reference electrode 28, which is made up of a strip conductor 31, an ion-selective membrane 32, a hydrogel electrolyte layer 34, and an enzyme layer 33 (starting from the surface of the substrate). In the variant of FIG. 11 the potentiometric reference electrode 28 is inside the cover membrane 30, whereas in that of FIG. 12 it is outside the cover membrane.

Figure 13:
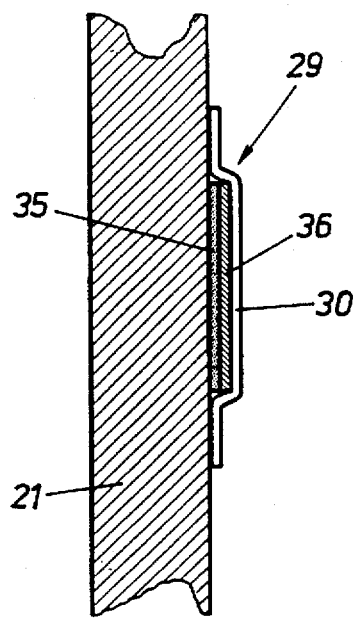
Figure 14:
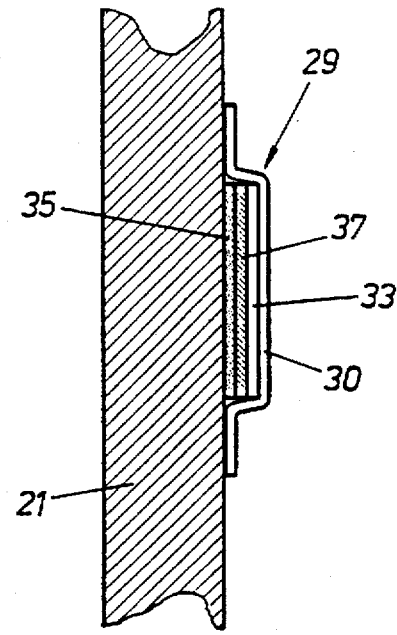
Figure 15:
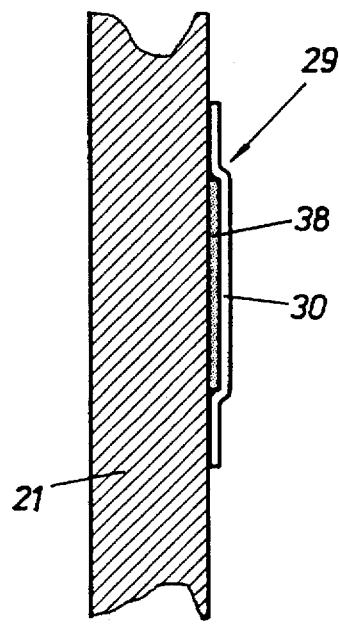
Figure 16:
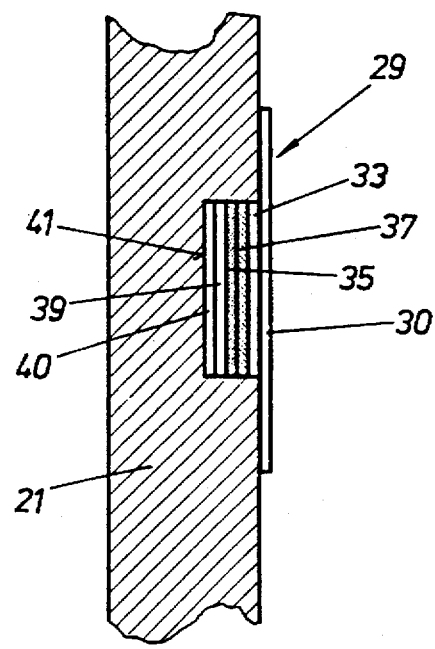

In FIGS. 13 to 16 variants of an optical biosensor are shown, comprising an optically transparent substrate 21 and an optode 29 of varying configuration. The optodes shown in this context may be integrated with amperometric or potentiometric sensors on a common substrate. In the variant of FIG. 13 the optode has an indicator layer 35 with an optical indicator component, and an enzyme layer 36 on top of the indicator layer 35, the enzyme layer 36 containing pigments for optical insulation of the indicator layer 35. As before, the cover layer 30 is sealed to the substrate 21 around the optode 29. In the variant of FIG. 14 the optical insulating layer 37 is outside the enzyme layer 33. A particularly simple variant is presented in FIG. 15, where the optode 29 is provided with a polymer matrix 38, in or on which the optical indicator and the biochemical component (e.g., an enzyme) are immobilized either chemically or physically. In the variant of FIG. 16 an optode 29 as in FIG. 14 (indicator layer 35, insulating layer 37, enzyme layer 33) is provided on a transparent foil 39, which is attached within a recess 41 of the transparent substrate 21 with the use of an optical coupling 40. The entire unit is covered by a plane cover membrane 30 and sealed around the sensor spot.

Figure 19:
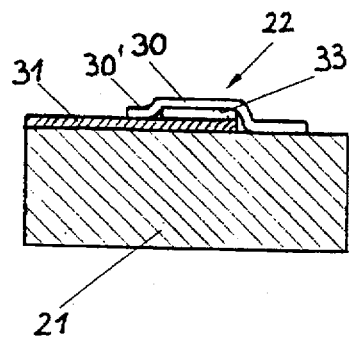
Figure 21:
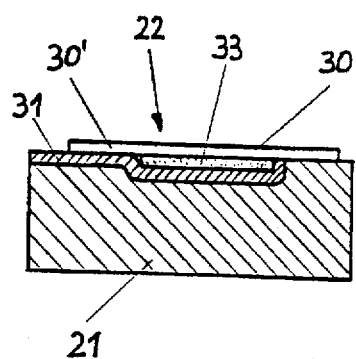
Figure 18:
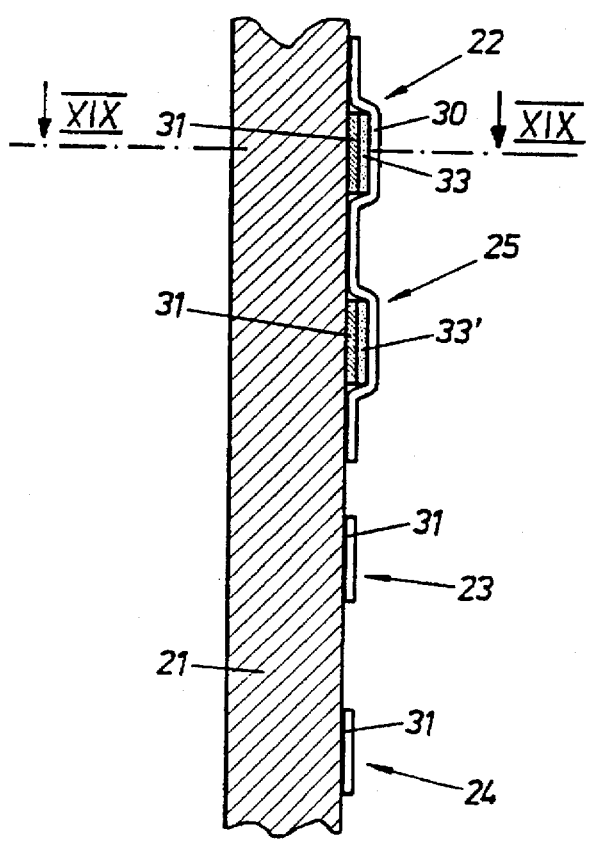
Figure 17:
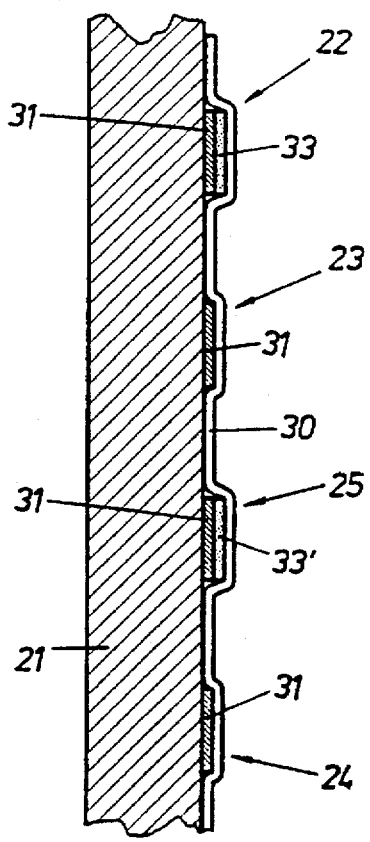

FIGS. 17 to 21 show different planar amperometric biosensors, the variants in FIGS. 17 and 18 being provided with reference and counterelectrodes 23, 24 in addition to working electrodes 22. FIG. 19 shows a section along line XIX—XIX in FIG. 18, and FIG. 21 shows a section along line XXI—XXI in FIG. 20, each in the area of the working electrode 22. The thermal seal of the cover membrane 30 is interrupted in the area 30' of the strip conductor 31 leading away from the sensor spots.

Figure 20:
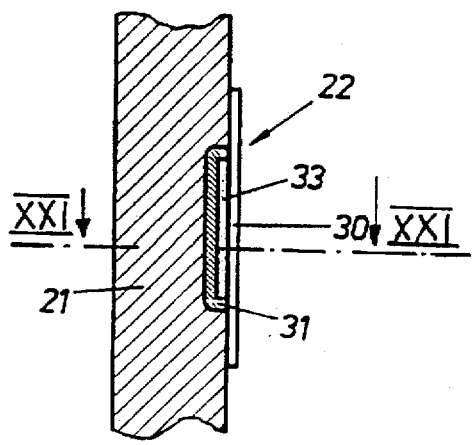

In the variants shown in FIGS. 17 and 18 a working electrode 22 and a comparison electrode 25 are provided on the substrate. The working electrodes have an active enzyme layer 33 on a strip conductor 31. The sensor spots of the comparison electrodes 25 are coated with an inactive enzyme layer 33'. In FIG. 17 all electrodes-are located under the cover membrane 30, in FIG. 18 only the working and reference electrodes 22, 25. Finally, the variant of FIG. 20 shows a working electrode sunk into the substrate 21, the strip conductor 31 surrounding the enzyme layer 33 and being covered by a flat cover membrane 30.

Following are examples of different biosensors with a sealed cover membrane prepared as described by the invention.

EXAMPLE A

Preparation of an amperometric glucose biosensor with a compensation electrode, based on an $H_2O_2$ transducer (FIGS. 4a, 4b, 17).

On a substrate 21 of polycarbonate the strip conductors 31 of the working electrodes 22 and the compensation electrode 25 are printed by a screen printing technique using a gold or platinum paste. The strip conductors 31 of the reference electrode 23 and the counterelectrode 24 are screen-printed with the use of an Ag/AgCl paste. On the strip conductor of the working electrode 22 a graphite or platinum paste with the active enzyme glucose oxidase immobilized thereon is applied as an enzyme layer 33 (FIG. 17), by a screen-printing and/or dispensing technique. The sensor spot for the compensation electrode 25 is prepared in the same way, with the exception of the glucose oxidase enzyme, which is replaced by cattle serum albumin or heat-deactivated glucose oxidase in this instance. As a cover membrane 30 a strip of polycarbonate foil (300 angstroms pore size) is applied, which is welded to the substrate by means of a sealing stamp (FIG. 4b) at 210° C. for 3 seconds at a pressure of 1.5 bar.

EXAMPLE B

Preparation of a potentiometric urea biosensor based on an ammonium electrode (FIG. 10).

On a substrate 21 of PMMA a strip conductor 31 is screen-printed, using a silver paste. On the side of the sample the same technique is employed for printing a solid contact layer 43 of graphite paste, followed by an insulating layer 44 of a polyurethane compound around the sensor spot and on top of the strip conductor. On the sensor spot itself a cocktail of PVC, a plasticizer (e.g., dioctyl adipate), the ionophor nonactin, and potassium-p-chlorotetraphenyl borate dissolved in tetrahydrofuran is applied dropwise (dispensing technique), and the solvent is evaporated. In this way an ammonium ion-selective membrane 32 is formed, on top of which the biochemical component 33 is applied dropwise from an aqueous solution, forming a hydrogel layer with covalent cross-linking. As top cover a polycarbonate membrane 30 is applied, with a pore size of 500 angstroms, which is sealed to the substrate at 185° C. for 3 seconds at a pressure of 1.5 bar. The sensor manufactured in this way may be used potentiometrically together with an external reference electrode.

EXAMPLE C

Preparation of a fluorescence-optical ascorbate biosensor based on an $O_2$ optode (FIG. 16).

On a transparent foil 39 of polyethylene terephthalate the optical indicator layer 35, i.e., the fluorescent dye decacyclene dissolved in a one-part silicone releasing acetic acid, is applied over a large area. As an optical insulating layer 37 a black-pigmented one-part silicone is applied, on which the enzyme ascorbic oxidase is immobilized by cross-linking with glutaric dialdehyde (enzyme layer 33). From the resulting laminate a sensor spot is cut and attached to the polycarbonate substrate 21 by means of a transparent two-part silicone adhesive, which is applied in the recess 41 as optical coupling 40, the thickness of the laminated foil corresponding to the depth of the recess 41 in the substrate. As a final step, a polycarbonate membrane of 500 angstroms pore size is sealed to the substrate around the optical sensor spot, at 210° C. for 3 seconds at a pressure of 1.5 bar.

We claim:

1. Planar sensor for determining a chemical parameter of a sample, comprising a substrate whose surface is at least partly plane and is provided with at least one potentiometric, amperometric or optical transducer, and at least one biochemical component said transducer and said biochemical component, being provided on said surface of said substrate or at least part of said surface as a sensor spot protected by a cover membrane which is gas and ion permeable and is heat welded to the surface of said substrate facing said sample forming a thermal seal, wherein those of said sensor spots that comprise a potentiometric or amperometric transducer are in contact with a strip conductor attached to said plane surface of said substrate, and wherein the thermal seal of said cover membrane is interrupted where said conducting stripes lead away from said sensor spots.

2. Sensor according to claim 1 with an amperometric arrangement, wherein at least one of said sensor spots is configured as a working electrode, and wherein at least one electrode from the group consisting of reference- and counterelectrodes is provided on said surface of said substrate.

3. Sensor according to claim 2, wherein said cover membrane additionally covers said electrode and is heat welded around said electrode to said substrate, the thermal seal being interrupted in an area of strip conductors leading away from said electrode.

4. Sensor according to claim 2, wherein an additional sensor spot with an optical transducer is provided which has an indicator layer with an optical indicator, and at least one layer with said biochemical component.

5. Sensor according to claim 2, wherein an additional sensor spot with a polymer matrix is provided, in or on which an optical indicator and said biochemical component are immobilized either chemically or physically.

6. Sensor according to claim 1 with a potentiometric arrangement, wherein at least one of said sensor spots is configured as a working electrode, and at least one reference electrode is provided on said surface of said substrate.

7. Sensor according to claim 6, wherein an additional sensor spot with an optical transducer is provided which has an indicator layer with an optical indicator, and at least one layer with said biochemical component.

8. Sensor according to claim 6, wherein an additional sensor spot with a polymer matrix is provided, in or on which an optical indicator and said biochemical component are immobilized either chemically or physically.

9. Sensor according to claim 1, wherein at least two sensor spots are provided, a first sensor spot serving as a working electrode and containing an active biochemical component, and a second sensor spot serving as a comparison electrode containing the same biochemical component in a deactivated state.

10. Sensor according to claim 1, wherein said cover membrane is a single layer.

11. Method of producing a planar sensor for determining a chemical parameter of a sample, said method including the steps of:
    (a) attaching a strip conductor to at least part of the surface of a substrate,
    (b) applying a potentiometric or amperometric transducer layer onto one end of said strip conductor,
    (c) affixing at least one biochemical component to said transducer layer,
    (d) covering at least said transducer layer and a surrounding area with a single gas and ion permeable cover membrane layer which is heat weldable to said substrate, and
    (e) thermally sealing said cover membrane to the substrate in areas not covered by said transducer later and said enzyme layer, the thermal seal being interrupted in the area of said strip conductor.

12. Method according to claim 11, wherein said cover membrane is unwound from a roll of tape, stretched over said surface of the substrate and thermally welded to said substrate by means of a heat stamp.

13. Method according to claim 11, wherein said cover membrane is thermally welded to said substrate by means of a laser technique.

14. Method according to claim 11, wherein said thermal seal obtained in step (e) is continuous.

15. Method according to claim 11, wherein said thermal seal obtained in step (e) is in individual spots.

16. Method of producing a planar sensor for stermining a chemical parameter of a sample, said method including the steps of:
    (a) attaching a strip conductor to at least part of the surface of a substrate,
    (b) applying a poller matrix on one end of said strip conductor,
    (c) immobilizing a potentiometric or amperometric transducer and a biochemical component on or in said polymer matrix,
    (d) covering at least aid transducer layer and a surrounding area with a single gas and ion permeable cover membrane layer which is weldable to said substrate, and
    (e) thermally sealing said cover membrane to said substrate in areas not covered by said transducer layer and said enzyme layer, the thermal seal being interrupted in the area of said strip conductor.

17. Method according to claim 16, wherein said cover membrane is unwound from a roll of tape, stretched over said surface of the substrate and thermally welded to said substrate by means of a heat stamp.

18. Method according to claim 16, wherein said cover membrane is thermally welded to said substrate by means of a laser technique.

19. Method according to claim 16, wherein said thermal seal obtained in step (e) is continuous.

20. Method according to claim 16, wherein said thermal seal obtained in step (e) is in individual spots.

* * * * *